(12) United States Patent
Friebe et al.

(10) Patent No.: US 6,506,755 B2
(45) Date of Patent: Jan. 14, 2003

(54) THIAZOLIDINECARBOXYL ACIDS

(75) Inventors: Walter-Gunar Friebe, Mannheim (DE); Hans-Willi Krell, Penzberg (DE); Sabine Woelle, Penzberg (DE); Hans-Peter Wolff, Weinheim (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/767,306

(22) Filed: Jan. 23, 2001

(65) Prior Publication Data

US 2002/0037901 A1 Mar. 28, 2002

(30) Foreign Application Priority Data

Feb. 3, 2000 (EP) .............................. 00102097

(51) Int. Cl.$^7$ .................... C07D 277/20; C07D 417/12; A61K 31/426; A61P 35/00
(52) U.S. Cl. .................. 514/252.05; 514/256; 514/369; 544/238; 544/335; 548/183
(58) Field of Search ................................ 544/335, 238; 548/183; 514/252.05, 256, 369

(56) References Cited

FOREIGN PATENT DOCUMENTS

| WO | 94 29287 | 12/1994 |
| WO | 94/29287 A1 * | 12/1994 |

OTHER PUBLICATIONS

Draetta, G. and Pagano, M. in "Annual Reports in Medicinal Chemistry, vol. 31", 1996, Academic Press, San Diego, p241–246.*
Rosenberg, S.. in "Annual Reports in Medicinal Chemistry, vol. 34", 1999, Academic Press, San Diego, p121–128..*
Behrendt, N. et al.; Fibrinolysis & Proteolysis, 12, pp. 191–204 (1998).
Andreasen P.A.; Int. J. Cancer, 72, pp. 1–22 (1997).
Hewitt R. et al.; Enzyme Protein, 49, pp. 163–173 (1996).

* cited by examiner

*Primary Examiner*—Richard L. Raymond
*Assistant Examiner*—Thomas McKenzie
(74) *Attorney, Agent, or Firm*—George W. Johnston; Robert A. Silverman

(57) ABSTRACT

5-Arylidene-4-oxo-2-thioxo-3-thiazolidinecarboxylic acids of formula I

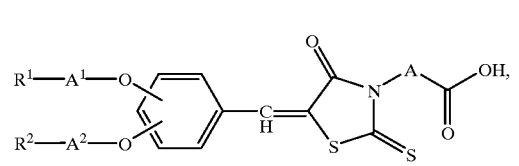

in which the symbols $R^1$, $R^2$, A, $A^1$ and $A^2$ have the significance given in the description as medicaments for the treatment of cancer diseases.

26 Claims, No Drawings

THIAZOLIDINECARBOXYL ACIDS

FIELD OF THE INVENTION

The object of the present invention are thiazolidinecarboxylic acids, a process for their manufacture and medicaments which contain these compounds as well as the use of these compounds in the production of medicaments.

BACKGROUND OF THE INVENTION

Plasmin is a key enzyme for the dissolution of the extracellular matrix, which occurs especially at contact sites of cells to an increasing extent. A strong expression of the uPA/uPAR system takes place especially in tumour cells (N. Behrendt et al., *Fibrinolysis & Proteolysis*, 1998, 12(4): The urokinase receptor). By the induction of the strong proteolytically active uPA(urokinase type Plasminogen Activator)/uPAR (membrane-bound urokinase receptor) system it is possible to spread the tumour cells in the body by dissolution of the extracellular matrix as a result of plasmin liberation (P. A. Andreasen et al., Int. J. Cancer, 1997,72: The urokinase-type plasminogen activator system in cancer metastasis: a review). A correlation of the increased expression rate of the uPA/uPAR system with an increased metastasing rate has been demonstrated in patients with different tumour diseases (e.g. R.Hewitt et al., *Enzyme Protein*, 1996,49: Stromal cell expression of components of matrix-degrading protease systems in human cancer). A significant reduction in tumour growth can be achieved in animal experiments with tumour cell lines in mice by blocking the uPAR system with monoclonal antibodies.

In the literature there are already described numerous 5-arylidene-rhodanine-carboxylic acids which differ from the compounds in accordance with the present invention in that the substitution of the phenyl ring differs distinctly from that of the present invention. IN particular, 5-(2,4-bis-benzyloxybenzylidene)rhodanineacetic acid and 5-(3,4-bis-benzyloxybenzylidene)-rhodanineacetic acid and their use for the prophylaxis of maturity onset diabetes are described in Patent Application DE 4318550. A connection between the prophylaxis of maturity onset diabetes and inhibiting the binding of uPA to uPAR, thereby preventing an activation of plasminogen to plasmin, does not exist. In fact, other compounds from Patent Application DE 4318550, which are especially valuable for the treatment of maturity onset diabetes, showed no activity in inhibiting the binding of uPA to uPAR, thereby preventing an activation of plasminogen to plasmin.

BRIEF SUMMARY OF THE INVENTION

The invention relates to a compound of formula I:

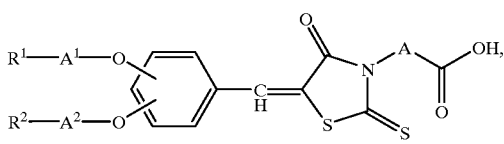

(I)

wherein
A is a linear $C_1$–$C_6$-alkyl chain or a group >CHR, wherein R is a $C_1$–$C_6$-alkyl residue, an aryl residue, an aralkyl residue or a carboxyalkyl residue,
$A^1$ and $A^2$
  each independently in any combination are a linear or branched saturated or unsaturated $C_1$–$C_6$-alkylene chain,
$R^1$ and $R^2$
  each independently in any combination are a group of formula II, formula III or formula IV,

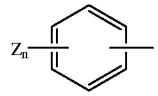

(II)

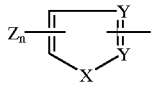

(III)

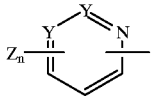

(IV)

wherein X is an oxygen or sulphur atom and each Y independently is a nitrogen or carbon atom, with the proviso that both Y's can not simultaneously be nitrogen,
Z is a $C_1$–$C_4$-alkyl, aryl, aralkyl, heteroaryl, heteroaralkyl, $C_3$–$C_5$-alkenyl, $C_1$–$C_4$-alkoxy, $C_1$–$C_4$-alkylthio, acylamino, (alkyl)aminocarbonyl, $C_1$–$C_4$-alkyl-carbonyl, trifluoromethyl, difluoromethoxy, trifluoromethoxy, trifluoromethylthio, nitro, hydroxy or carboxy group or a chlorine, bromine or fluorine atom
  or the aromatic ring in formulae II-IV is substituted with a methylenedioxy or ethylenedioxy group and
n is a whole number between 0 and 3,
whereby the Z substituents can be present in any positions, with the proviso that the $R^1$-$A^1$- and $R^2$-$A^2$-residues can not simultaneously be an unsubstituted benzyl residue when A is a methylene group, or a
pharmaceutically acceptable salt or ester of a compound of formula I, or a position isomer, optically active form, racemate or diastereomer mixture thereof.

In another aspect, the invention relates to a method of preventing tumour growth or metastasis, comprising administering to a patient in need of such treatment or prevention an effective amount of a compound of formula I,

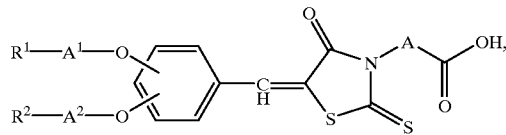

(I)

in which
A is a linear $C_1$–$C_6$-alkylene chain or a group >CHR, wherein R is a $C_1$–$C_6$-alkyl residue, an aryl residue, an aralkyl residue or a carboxyalkyl residue,
$A^1$ and $A^2$
  each independently in any combination are a linear or branched saturated or unsaturated $C_1$–$C_6$-alkylene chain,
$R^1$ and $R^2$
  each independently in any combination are a group of formula II, formula III or formula IV,

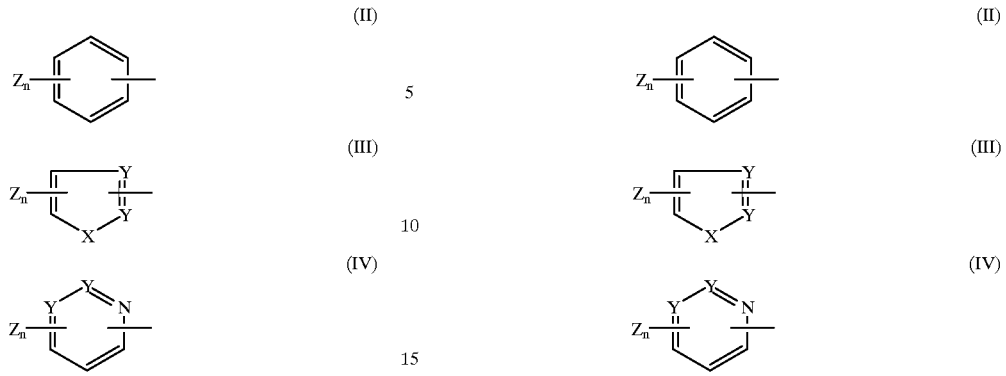

wherein X is an oxygen or sulphur atom and each Y is a nitrogen or carbon atom, with the proviso that both Y's can not simultaneously be nitrogen, Z is a $C_1$–$C_4$-alkyl, aryl, aralkyl, heteroaryl, heteroaralkyl, $C_3$–$C_5$-alkenyl, $C_1$–$C_4$-alkoxy, $C_1$–$C_4$-alkylthio, acylamino, (alkyl)aminocarbonyl, $C_1$–$C_4$-alkyl-carbonyl, trifluoromethyl, difluoromethoxy, trifluoromethoxy, trifluoromethylthio, nitro, hydroxy or carboxy group or a chlorine, bromine or fluorine atom or the aromatic ring in formulae II-IV is substituted with a methylenedioxy or ethylenedioxy group and n is a whole number between 0 and 3, whereby the Z substituents can be present in any positions, or a pharmaceutically acceptable salt or ester of a compound of formula I, or a position isomer, optically active form, racemate or diastereomer mixture thereof.

DETAILED DESCRIPTION OF THE INVENTION

The invention is concerned with the use of 5-arylidene-4-oxo-2-thioxo-3-thiazolidine-carboxylic acids of formula I

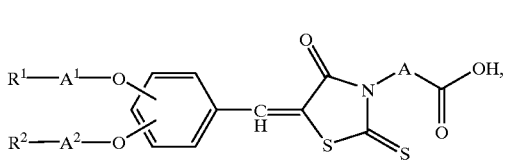

(I)

as medicaments for the treatment of cancer diseases, especially for the prevention of the growth and the metastasing of tumors, in which A signifies a linear $C_1$–$C_6$-alkylene chain or a group >CHR, wherein R signifies a $C_1$–$C_6$-alkyl residue, an aryl residue, an aralkyl residue or a carboxyalkyl residue, $A^1$ and $A^2$ each independently in any combination signify a linear or branched saturated or unsaturated $C_1$–$C_6$-alkylene chain, $R^1$ and $R^2$ each independently in any combination signify a group of general formula II to IV, wherein X signifies an oxygen or sulphur atom and each Y independently signifies a nitrogen or carbon atom, with the proviso that both Y's can not simultaneously signify nitrogen, Z signifies a $C_1$–$C_4$-alkyl, aryl, aralkyl, heteroaryl, heteroaralkyl, $C_3$–$C_5$-alkenyl, $C_1$–$C_4$-alkoxy, $C_1$–$C_4$-alkylthio, acylamino, (alkyl)aminocarbonyl, $C_1$–$C_4$-alkyl-carbonyl, trifluoromethyl, difluoromethoxy, trifluoromethoxy, trifluoromethylthio, nitro, hydroxy or carboxy group or a chlorine, bromine or fluorine atom or the aromatic ring in formulae II-IV is substituted with a methylenedioxy or ethylenedioxy group and n is a whole number between 0 and 3, whereby the Z substituents can be present in any positions, as well as compounds of formula I in which the symbols A, $R^1$, $R^2$, $A^1$, $A^2$, Z and n have the significance set forth above, with the proviso that the $R^1$-$A^1$- and $R^2$-$A^2$- residues can not simultaneously signify an unsubstituted benzyl residue when A is a methylene group, and their use as medicaments for the treatment of cancer diseases, especially for the prevention of the growth and the metastasing of tumours.

Objects of this invention are also physiologically compatible salts or esters of formula I as well as the position isomers, the optically active forms, the racemates and the diastereomer mixtures of these compounds.

It has surprisingly been found that the compounds of formula I have valuable pharmacological properties. In particular, they inhibit the binding of uPA (urokinase type Plasminogen Activator) to the membrane-bound urokinase receptor (uPAR) and thereby prevent an activation of plasminogen to plasmin.

Accordingly, the compounds in accordance with the invention are valuable, low molecular weight, orally administerable medicaments for the prophylaxis and treatment of cancer diseases, which are especially suitable for preventing the growth and the metastasing of tumours.

In formulae I-IV the $C_1$–$C_4$-alkyl residues, the $C_1$–$C_6$-alkyl residues and the $C_3$–$C_5$-alkenyl residues can be straight-chain or branched. Preferably, the methyl, ethyl, propyl, isopropyl, butyl, isobutyl, tert.butyl, pentyl, hexyl, allyl and isopropenyl residues are to be understood thereunder.

As $C_1$–$C_6$-alkylene chains of residues $A^1$ and $A^2$ there preferably come into consideration the methylene, the 1,2-ethanediyl, the 1,3-propanediyl and the 1,4-butanediyl group.

The groups of formula III are preferably thienyl, furanyl, isoxazolyl, thiazolyl and oxazolyl. The groups of formula IV are preferably pyridinyl and pyrimidinyl.

As the alkyl residue in the Z substituents there is to be understood lower alkyl with 1–4 carbon atoms, especially the methyl, ethyl, isopropyl and tert.butyl residue. Preferred Z residues are, furthermore, the phenyl, 2-thienyl, 3-thienyl, methoxy, trifluoromethyl, trifluoromethoxy, methylthio and acylamino groups as well as the halogen atoms chlorine, fluorine and bromine. Acyl residues are preferably acetyl and propionyl. The phenyl and thienyl residues can be substituted with one or two residues, whereby these residues can be the same as or different to one another and can be a lower alkyl, lower alkoxy, nitro, (di)(alkyl)amino, trifluoromethyl or hydroxy group or halogen. Under halogen there is to be understood here fluorine, bromine and especially chlorine.

Under the $C_1$–$C_6$-alkylene chains of residue A there are to be understood especially the methylene, the 1,2-ethanediyl, the 1,3-propanediyl and the 1,4-butanediyl residue.

An aryl residue present as the substituent R in >CH(R) for A signifies phenyl which can be unsubstituted or substituted with one or two residues, whereby these residues can be the same as or different to one another and can be a lower alkyl group, lower alkoxy group, hydroxy group or halogen. Under halogen there is to be understood here fluorine, bromine and especially chlorine. Aralkyl for the same substituent denotes an aryl residue as previously defined linked by a $C_1$–$C_6$-alkylene group as defined above. A carboxyalkyl residue preferably signifies the group —$(CH_2)_m$—COOH and m=1–3.

Preferred compounds of formula I are compounds in which A is either a linear $C_1$–$C_6$-alkylene chain or a group >CH(R), whereby the compounds in question can be present in the (R) or (S) configuration or as the racemate when R signifies a linear $C_1$–$C_6$-alkyl residue, an aryl residue, an aralkyl residue or a carboxyalkyl residue.

Preferred compounds are, furthermore, compounds in which $R^1$-$A^1$- and $R^2$-$A^2$- are the same as or different to one another and in each case signify an aralkyl group with a $C_1$–$C_4$-alkylene chain, a cinnamyl residue, a 2-thienylmethyl, a 3-thienylmethyl, a 2-furanylmethyl, a 3-furanylmethyl, a 2-thiazolylmethyl, a 4-thiazolylmethyl, a 2-oxazolylmethyl, a 4-oxazolyl-methyl, a 3-isoxazolylmethyl or a 4-isoxazolylmethyl group or homologue thereof with $C_2$–$C_4$-alkylene chains, whereby the respective aryl and heteroaryl residues of the aforementioned groups can be mono- or multiply-substituted by one of the Z substituents defined above.

Especially preferred sub-groups of compounds of general formula I are compounds in which $R^1$ and $R^2$ each independently signify benzyl groups, 2-phenethyl groups, 3-phenyl-propyl groups or groups of general formulae III and IV, wherein the groups $A^1$ and $A^2$ are methylene, 1,2-ethanediyl or 1,3-propanediyl and A signifies methylene, phenylmethylene, 2-phenylethane-1,1-diyl, 1,2-ethanediyl or 1,3-propanediyl, whereby the aryl and heteroaryl groups are optionally substituted by the Z substituents set forth above.

Examples of physiologically usable salts of the compounds of formula I are salts with physiologically compatible bases. Examples of such salts are alkali metal, alkaline earth metal, ammonium and alkylammonium salts, such as the Na, K, Ca or tetramethylammonium salt.

The separation of the racemates into the enantiomers can be carried out by analytical, semi-preparative and preparative chromatography on suitable optically active phases with conventional elution agents.

Suitable optically active phases are, for example, optically active polyacrylamides or polymethacrylamides and to some extent also silica gel (e.g. ChiraSpher® from Merck, Chirapak® OT/OP from Baker), cellulose esters/carbamates (e.g. Chiracel® OB/OY from Baker/Diacel), phases based on cyclodextrins or crown ethers (e.g. Crownpak® from Diacel) or microcrystalline cellulose triacetate (Merck).

Enantiomers of compounds of formula I can also be obtained by using the respective optically active starting material for the synthesis of the compounds.

The compounds of general formula I in which $R^1$, $R^2$, A, $A^1$, $A^2$, Z and n have the significances set forth above are manufactured by condensing an aromatic aldehyde of formula V

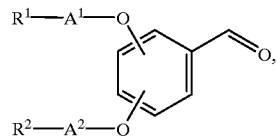

(V)

in which $R^1$, $R^2$, $A^1$ and $A^2$ have the significances set forth above, with a rhodaninecarboxylic acid derivative of formula VI

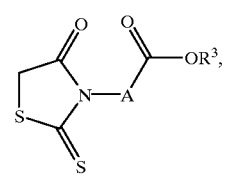

(VI)

in which A has the significance set forth above and $R^3$ signifies hydrogen or a lower alkyl residue,
in a known manner known to give a compound of formula I or VII

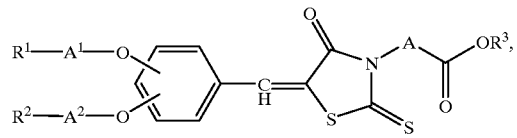

(VII)

and, if desired, saponifying the ester group $OR^3$ in a compound of formula VII according to known methods.

The condensation is usually carried out in the presence of a catalytic amount of a base such as sodium acetate or pyridine. In accordance with the invention piperidine acetate is used as the catalyst under water-withdrawing conditions, for example in the presence of water-binding reagents such as molecular sieve or sodium sulphate or by azeotropic withdrawal of water.

The saponification of an ester of formula VII can be carried out not only under acidic conditions, but also under basic conditions. Preferably, the esters are saponified by treatment with 1N potassium hydroxide solution in methanol at 40° C.

A further known method for the manufacture of the compounds of formula I in which $R^1$, $R^2$, A, $A^1$, $A^2$, Z and n have the significances set forth above comprises the condensation of compounds of formula V with rhodanine to give compounds of formula VIII

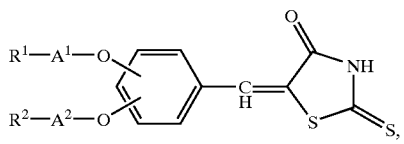

and subsequent alkylation with compounds of formula IX

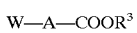

in which W signifies a reactive group such as chlorine, bromine, methylsulphonyloxy or p-toluenesulphonyloxy and R³ has the significance given above, to give compounds of formula I or VII.

The alkylations are usually carried out with the addition of an acid-binding agent such as e.g. sodium acetate, triethylamine or potassium carbonate in a polar or non-polar solvent, preferably in dimethylformamide or methylene chloride, at temperatures between −40° C. and the boiling point of the chosen solvent. Preferably, an alkali salt of compounds of formula VIII and a free acid of formula IX, wherein W signifies bromine or chlorine and R³ signifies hydrogen, are used for the alkylation in the presence of excess alkali.

The preparation of aldehydes of formula V is effected according to methods known from the literature, such as e.g. the optionally selective alkylation of dihydroxyalkylbenzaldehydes, as described by e.g. von Reichstein et al. in Helv. Chim. Acta 18, 816 (1935).

The compounds of formula VI are commercially available or can be prepared according to conventional processes known from the literature.

For the production of medicaments, the compounds of formula I can be mixed in a manner known per se with suitable pharmaceutical carrier substances, aromas, flavorants and colorants and formed, for example, as tablets or dragées or suspended or dissolved in water or oil, e.g. olive oil, with the addition of appropriate adjuvants.

The thiazolidinecarboxylic acids of formula I can be administered orally and parenterally in liquid or solid form. As the injection medium there is preferably used water which contains stabilizing agents, solubilizers and/or buffers which are usual in the case of injection solutions. Such additives are e.g. tartrate or borate buffer, ethanol, dimethyl sulphoxide, complex formers (such as ethylenediaminetetraacetic acid), high molecular weight polymers (such as liquid polyethylene oxide) for viscosity adjustment or polyethylene derivatives of sorbitan hydrides.

Solid carrier materials are e.g. starch, lactose, mannitol, methylcellulose, talc, highly dispersed silicic acid and high molecular weight polymers (such as polyethylene glycols). If desired, preparations suitable for oral administration can contain flavorants and sweeteners.

The dosage administered depends on the age, the health and the weight of the recipient, the extent of the disease, the additional treatments which may be carried out simultaneously by the physician and the kind of effect which is desired. Usually, the daily dosage of active compound amounts to 0.1 to 50 mg/kg body weight. Normally, 0.5 to 40 mg/kg/day, preferably 1.0 to 20 mg/kg/day, in one or more doses are effective in achieving the desired results. The active agent can be given in the form of tablets, capsules or injections.

The following compounds of formula I are especially preferred in the scope of the present invention in addition to those set forth in the Examples:

1. 5-[(2,4-Bis-(4-chlorophenylmethoxy)phenyl)methylene]-4-oxo-2-thioxo-3-thiazolidine-acetic acid
2. 5-[(2,4-Bis-(4-methylphenylmethoxy)phenyl)methylene]-4-oxo-2-thioxo-3-thiazolidineacetic acid Fp=211° C.
3. 5-[(2,4-Bis-(3,4-methylenedioxyphenylmethoxy)phenyl)methylene]-4-oxo-2-thioxo-3-thiazolidineacetic acid
4. 5-[(2,4-Bis-(2-chlorophenylmethoxy)phenyl)methylene]-4-oxo-2-thioxo-3-thiazolidineacetic acid
5. 5-[(2,4-Bis-(3-chlorophenylmethoxy)phenyl)methylene]-4-oxo-2-thioxo-3-thiazolidineacetic acid
6. 5-[(2,4-Bis-(3-(4-chlorophenyl)propoxy)phenyl)methylene]-4-oxo-2-thioxo-3-thiazolidineacetic acid
7. 5-[(2,4-Bis-(4-methoxyphenylmethoxy)phenyl)methylene]-4-oxo-2-thioxo-3-thiazolidineacetic acid
8. 5-[(2,4-Bis-(2-phenylethoxy)phenyl)methylene]-4-oxo-2-thioxo-3-thiazolidine-acetic acid
9. 5-[(2,4-Bis-(3-phenylpropoxy)phenyl)methylene]-4-oxo-2-thioxo-3-thiazolidine-acetic acid
10. 5-[(2-Phenylmethoxy-4-(3-phenylpropoxy)phenyl)methylene]-4-oxo-2-thioxo-3-thiazolidineacetic acid
11. 5-[(2-(4-Chlorophenylmethoxy)-4-(3-phenylpropoxy)phenyl)methylene]-4-oxo-2-thioxo-3-thiazolidineacetic acid
12. 5-[(2-(2-Thienylmethoxy)-4-(3-phenylpropoxy)phenyl)methylene]-4-oxo-2-thioxo-3-thiazolidineacetic acid
13. 5-[(2-(2-Pyridylmethoxy)-4-(3-phenylpropoxy)phenyl)methylene]-4-oxo-2-thioxo-3-thiazolidineacetic acid
14. 2-{5-[(2,4-Bis-benzyloxyphenyl)methylene]-4-oxo-2-thioxo-3-thiazolidine}-propionic acid
15. 1-{5-[(2,4-Bis-benzyloxyphenyl)methylene]-4-oxo-2-thioxo-3-thiazolidine}-propionic acid
16. {5-[(2,4-Bis-benzyloxyphenyl)methylene]-4-oxo-2-thioxo-3-thiazolidine}-phenyl-acetic acid
17. {5-[(2,5-Bis-benzyloxyphenyl)methylene]-4-oxo-2-thioxo-3-thiazolidine}-phenyl-acetic acid
18. {5-[(2,5-Bis-benzyloxyphenyl)methylene]-4-oxo-2-thioxo-3-thiazolidine}-(4-chloro-phenyl)-acetic acid
19. 4-{5-[(2,4-Bis-benzyloxyphenyl)methylene]-4-oxo-2-thioxo-3-thiazolidine}-butyric acid
20. 2-{5-[(2,4-Bis-benzyloxyphenyl)methylene]-4-oxo-2-thioxo-3-thiazolidine}-3-phenyl-butyric acid
21. 2-{5-[(2,5-Bis-benzyloxyphenyl)methylene]-4-oxo-2-thioxo-3-thiazolidine}-3-phenyl-butyric acid
22. 5-[(2-Benzyloxy-4-(2-phenyl-5-methyl-4-oxazolylethoxy)phenyl)methylene]-4-oxo-2-thioxo-3-thiazolidineacetic acid
23. 5-[(2-(4-Chlorophenylmethoxy)-4-(2-phenyl-5-methyl-4-oxazolylethoxy)phenyl)-methylene]-4-oxo-2-thioxo-3-thiazolidineacetic acid
24. 5-[(2-(2-Thienylmethoxy)-4-(2-phenyl-5-methyl-4-oxazolylethoxy)phenyl)methylene]-4-oxo-2-thioxo-3-thiazolidineacetic acid
25. 5-[(2-(2-Pyridylmethoxy)-4-(2-phenyl-5-methyl-4-oxazolylethoxy)phenyl)methylene]-4-oxo-2-thioxo-3-thiazolidineacetic acid.

EXAMPLE 1

5-[(2,5-Bis-(4-chlorophenylmethoxy)phenyl)methylene]-4-oxo-2-thioxo-3-thiazolidineacetic Acid 125 mg (0.323 mmol) of 2,5-bis-(4-chlorophenylmethoxy)benzaldehyde, 68.3 mg (0.355 mmol) of rhodanine-3-acetic acid, 18 mg (0.125 mmol) of piperidine acetate and 10 ml of toluene were heated on a water separator under a nitrogen atmosphere for 4 hours. Subsequently, the reaction mixture was evaporated, the residue was taken up in ethyl acetate, washed several times with water, dried and again evaporated. The residue was triturated with diethyl ether and filtered off under suction: 125 mg (69%) of the title compound; $^1$HNMR (DMSO-d6, 250 MHz) δ 7.92 (s, 1H), 7.49 (m, 8H), 7.20 (m, 2H), 7.00 (m, 1H), 5.22 (s, 2H), 5.18 (s, 2H), 4.57 (s, 2H); TLC (toluene/methyl ethyl ketone/glacial acetic acid (72:20:8)): Rf=0.51.

EXAMPLE 2

5-[(2,5-Bis-(4-methylphenylmethoxy)phenyl) methylene]-4-oxo-2-thioxo-3-thiazolidineacetic Acid Analogously to Example 1, from rhodanineacetic acid and 2,5-bis-(4-methylphenylmethoxy)-benzaldehyde, yield 50%.

$^1$HNMR (DMSO-d6, 250 MHz) δ 7.95 (s, 1H), 6.95–7.40 (m, 11H), 5.16 (s, 2H), 5.10 (s, 2H), 4.70 (s, 2H), 2.30 (2xs, 6H); TLC (toluene/methyl ethyl ketone/glacial acetic acid (72:20:8)): Rf=0.53.

EXAMPLE 3

5-[(2,5-Bis-(3,4-methylenedioxyphenylmethoxy) phenyl)methylene]-4-oxo-2-thioxo-3-thiazolidineacetic Acid Analogously to Example 1 from rhodanineacetic acid and 2,5-bis-(3,4-methylenedioxy-phenyl-methoxy) benzaldehyde, yield 79%.

$^1$HNMR (DMSO-d6, 250 MHz) δ 7.92 (s, 1H), 6.85–7.20 (m, 9H), 6.00 (2xs, 4H), 5.10 (s, 2H), 5.01 (s, 2H), 4.60 (s, 2H); TLC (toluene/methyl ethyl ketone/glacial acetic acid (72:20:8)): Rf=0.52.

EXAMPLE 4

5-[(2,5-Bis-(2-chlorophenylmethoxy)phenyl) methylene]-4-oxo-2-thioxo-3-thiazolidineacetic Acid Analogously to Example 1, from rhodanineacetic acid and 2,5-bis-(2-chlorophenyl-methoxy)-benzaldehyde, yield 86%.

$^1$HNMR (DMSO-d6, 250 MHz) δ 8.00 (s, 1H), 6.95–7.65 (m, 11H), 5.29 (s, 2H), 5.21 (s, 2H), 4.70 (s, 2H); TLC (toluene/methyl ethyl ketone/glacial acetic acid (72:20:8)): Rf=0.60.

EXAMPLE 5

5-[(2,5-Bis-(3-chlorophenylmethoxy)phenyl) methylene]-4-oxo-2-thioxo-3-thiazolidineacetic Acid Analogously to Example 1, from rhodanineacetic acid and 2,5-bis-(3-chlorophenyl-methoxy)-benzaldehyde, yield 71%.

$^1$HNMR (DMSO-d6, 250 MHz) δ 8.00 (s, 1H), 6.95–7.52 (m, 11H), 5.22 (s, 2H), 5.19 (s, 2H), 4.71 (s, 2H); TLC (toluene/methyl ethyl ketone/glacial acetic acid (72:20:8)): Rf=0.58.

EXAMPLE 6

5-[(2,5-Bis-(3-(4-chlorophenyl)propoxy)phenyl) methylene]-4-oxo-2-thioxo-3-thiazolidine-acetic Acid Analogously to Example 1, from rhodanineacetic acid and 2,5-bis-(3-(4-chlorophenyl)-propoxy)benzaldehyde, yield 53%.

$^1$HNMR (DMSO-d6, 250 MHz) δ 8.01 (s, 1H), 6.90–7.70 (m, 11H), 4.75 (s, 2H), 4.08 (t, 2H), 3.98 (t, 2H), 2.74 (2μt, 4H), 2.03 (m, 4H); TLC (toluene/methyl ethyl ketone/ glacial acetic acid (72:20:8)): Rf=0.67.

EXAMPLE 7

5-[(3,4-bis-(4-chlorophenylmethoxy)phenyl) methylene]-4-oxo-2-thioxo-3-thiazolidineacetic Acid Analogously to Example 1, from rhodanineacetic acid and 3,4-bis-(4-chlorophenyl-methoxy)-benzaldehyde, yield 68%.

$^1$HNMR (DMSO-d6, 250 MHz) δ 7.79 (s, 1H), 6.75–7.55 (m, 11H), 5.24 (s, 2H), 5.22 (s, 2H), 4.72 (s, 2H); TLC (toluene/methyl ethyl ketone/glacial acetic acid (72:20:8)): Rf=0.54.

EXAMPLE 8

5-[(2,5-Bis-(4-methoxyphenylmethoxy)phenyl) methylene]-4-oxo-2-thioxo-3-thiazolidine-acetic Acid Analogously to Example 1, from rhodanineacetic acid and 2,5-bis-(4-methoxyphenyl-methoxy)benzaldehyde, yield 79%.

$^1$HNMR (DMSO-d6, 250 MHz) δ 7.95 (s, 1H), 6.80–7.50 (m, 11H), 5.11 (s, 2H), 5.06 (s, 2H), 4.70 (s, 2H), 3.75 (2xs, 6H); TLC (toluene/methyl ethyl ketone/glacial acetic acid (72:20:8)): Rf=0.62.

EXAMPLE 9

5-[(2,5-Bis-(2-phenylethoxy)phenyl)methylene]-4-oxo-2-thioxo-3-thiazolidineacetic Acid Analogously to Example 1, from rhodanineacetic acid and 2,5-bis-(2-phenyl-ethoxy)-benzaldehyde, yield 53%.

$^1$HNMR (DMSO-d6, 250 MHz) δ 7.93 (s, 1H), 6.85–7.30 (m, 13H), 4.75 (s, 2H), 4.10–4.35 (2xt, 4H), 2.95–3.15 (2xt, 4H); TLC (toluene/methyl ethyl ketone/glacial acetic acid (72:20:8)): Rf=0.50.

EXAMPLE 10

5-[(2,5-Bis-(3-phenylpropoxy)phenyl)methylene]-4-oxo-2-thioxo-3-thiazolidineacetic acid Analogously to Example 1, from rhodanineacetic acid and 2,5-bis-(3-phenyl-propoxy)-benzaldehyde, yield 44%.

$^1$HNMR (DMSO-d6, 250 MHz) δ 8.02 (s, 1H), 6.90–7.38 (m, 13H), 4.73 (s, 2H), 4.08 (t, 2H), 3.98 (t, 2H), 2.75 (2xt, 4H), 2.08 (m, 4H); TLC (toluene/methyl ethyl ketone/glacial acetic acid (72:20:8)): Rf=0.52.

EXAMPLE 11

5-[(2.3-Bis-(3-phenylpropoxy)phenyl)methylene]-4-oxo-2-thioxo-3-thiazolidineacetic Acid Analogously to Example 1, from rhodanineacetic acid and 2.3-bis-(3-phenyl-propoxy)-benzaldehyde, yield 34%.

$^1$HNMR (DMSO-d6, 250 MHz) δ 8.06 (s, 1H), 7.00–7.40 (m, 13H), 4.56 (s, 2H), 4.07 (t, 2H), 4.01 (t, 2H), 2.65–2.90 (2xt, 4H), 1.95–2.20 (m, 4H); TLC (toluene/methyl ethyl ketone/glacial acetic acid (72:20:8)): Rf=0.50.

EXAMPLE 12

5-[(3,4-bis-(3-phenylpropoxy)phenyl)methylene]-4-oxo-2-thioxo-3-thiazolidineacetic Acid Analogously to Example 1, from rhodanineacetic acid and 3,4-bis-(3-phenyl-propoxy)-benzaldehyde, yield 68%.

¹HNMR (DMSO-d6, 250 MHz) δ 7.85 (s, 1H), 7.10–7.35 (m, 13H), 4.72 (s, 2H), 4.00–4.20 (m, 4H), 2.70–2.90 (m, 4H), 1.95–2.15 (m, 4H); TLC (toluene/methyl ethyl ketone/glacial acetic acid (72:20:8)): Rf=0.65.

EXAMPLE 13

5-[(2-Phenylmethoxy-5-(3-phenylpropoxy)phenyl)methylene]-4-oxo-2-thioxo-3-thiazolidineacetic Acid Analogously to Example 1, from rhodanineacetic acid and 2-phenylmethoxy-5-(3-phenyl-propoxy)benzaldehyde, yield 72%.

¹HNMR (DMSO-d6, 250 MHz) δ 8.01 (s, 1H), 6.95–7.40 (m, 13H), 5.15 (s, 2H), 4.72 (s, 2H), 4.08 (t, 2H), 2.75 (t, 2H), 2.00–2.15 (m, 2H); TLC (toluene/methyl ethyl ketone/glacial acetic acid (72:20:8)): Rf=0.62.

EXAMPLE 14

5-[(2-(4-Chlorophenylmethoxy)-5-(3-phenylpropoxy)phenyl)methylene]-4-oxo-2-thioxo-3-thiazolidineacetic Acid Analogously to Example 1, from rhodanineacetic acid and 2-(4-chlorophenylmethoxy)-5-(3-phenyl-propoxy)benzaldehyde, yield 90%.

¹HNMR (DMSO-d6, 250 MHz) δ 8.01 (s, 1H), 6.90–7.55 (m, 12H), 5.14 (s, 2H), 4.75 (s, 2H), 4.08 (t, 2H), 2.75 (t, 2H) 2.00–2.15 (m, 2H); TLC (toluene/methyl ethyl ketone/glacial acetic acid (72:20:8)): Rf=0.56.

EXAMPLE 15

5-[(2-(2-Thienylmethoxy)-5-(3-phenylpropoxy)phenyl)methylene]-4-oxo-2-thioxo-3-thiazolidineacetic Acid Analogously to Example 1, from rhodanineacetic acid and 2-(2-thienylmethoxy)-5-(3-phenyl-propoxy)benzaldehyde, yield 78%.

¹HNMR (DMSO-d6, 250 MHz) δ 8.05 (s, 1H), 6.65–7.68 (m, 11H), 5.37 (s, 2H), 4.76 (s, 2H), 4.10 (m, 2H), 2.78 (m, 2H), 2.00–2.20 (m, 2H); TLC (toluene/methyl ethyl ketone/glacial acetic acid (72:20:8)): Rf=0.53.

EXAMPLE 16

5-[(2-(2-Pyridylmethoxy)-5-(3-phenylpropoxy)phenyl)methylene]-4-oxo-2-thioxo-3-thiazolidineacetic Acid Analogously to Example 1, from rhodanineacetic acid and 2-(2-pyridylmethoxy)-5-(3-phenylpropoxy)benzaldehyde, yield 15%.

Low resolution mass spectroscopy (ES) m/e 521 (MH+); TLC (toluene/methyl ethyl ketone/glacial acetic acid (72:20:8)): Rf=0.56.

EXAMPLE 17

3-{5-[(2,5-Bis-benzyloxyphenyl)methylene]-4-oxo-2-thioxo-3-thiazolidinel}-propionic Acid a) 5-[(2,5-Bis-benzyloxyphenyl)methylene]-4-oxo-2-thioxo-thiazolidine 1.59 g (5 mmol) of 2,5-bis-benzyloxybenzaldehyde, 0.73 g (5.5 mmol) of rhodanine, 0.29 g (2 mmol) of piperidine acetate and 40 ml of toluene were heated on a water separator under a nitrogen atmosphere for 1.5 hours. After cooling, the yellow crystals were filtered off under suction, washed with toluene and diethyl ether and dried in a vacuum: 1.34 g (62%) of 5-[(2,5-bis-benzyloxyphenyl)methylene]-4-oxo-2-thioxo-thiazolidine; ¹HNMR (DMSO-d6, 250 MHz) δ 13.80 (s, 1H), 7.80 (s, 1H), 6.85–7.50 (m, 13H), 5.19 (s, 2H), 5.10 (s, 2H); TLC (toluene/methyl ethyl ketone/glacial acetic acid (72:20:8)): Rf=0.80.

b) Title Compound

A mixture of 130 mg (0.3 mmol) of 5-[(2,5-bis-benzyloxyphenyl)methylene]-4-oxo-2-thioxo-thiazolidine, 194 mg (0.7 mmol) of potassium carbonate, 92 mg (0.6 mmol) of 3-bromo-propionic acid and 2 ml of dimethylformamide was stirred at 50° C. for 2.5 hours. After cooling the mixture was treated with water and acidified with dilute hydrochloric acid. The precipitate was filtered off, triturated under isopropanol and dried: 54 mg (36%) of the title compound; ¹HNMR (DMSO-d6,250 MHz) δ 7.94 (s, 1H), 6.85–7.60 (m, 13H), 5.20 (s, 2H), 5.12 (s, 2H), 4.20 (m, 2H), 2.60–2.80 (m 2H); TLC (toluene/methyl ethyl ketone/glacial acetic acid (72:20:8)): Rf=0.60.

EXAMPLE 18

4-{5-[(2,5-Bis-benzyloxyphenyl)methylene]-4-oxo-2-thioxo-3-thiazolidine}-butyric Acid Analogously to Example 18b, from 5-[(2,5-bis-benzyloxyphenyl)methylene]-4-oxo-2-thioxo-thiazolidine and 4-brombutyric acid, yield 45%.

¹HNMR (DMSO-d6, 250 MHz) δ 7.94 (s, 1H), 6.90–7.50 (m, 13H), 5.20 (s, 2H), 5.16 (s, 2H), 3.95–4.10 (m, 2H), 2.20–2.40 (m, 2H), 1.70–2.00 (m, 2H); TLC (toluene/methyl ethyl ketone/glacial acetic acid (72:20:8)): Rf=0.62.

EXAMPLE 19

2-{5-[(2,5-Bis-(4-methylphenylmethoxy)phenyl)methylene]-4-oxo-2-thioxo-3-thiazolidine}-3-phenylpropionic Acid Analogously to Example 1, from 2,5-bis-(4-methylphenylmethoxy)benzaldehyde and 2-(4-oxo-2-thioxo-3-thiazolidine)-3-phenylpropionic acid, yield 90%.

¹HNMR (DMSO-d6, 250 MHz) δ 7.9 (s, 1H), 6.8–7.4 (m, 16H), 5.85 (m, 1H), 5.15 (s, 2H), 5.05 (s, 2H), 3.5 (m, 2H), 2.5 (s, 3H), 2.3 (s, 3H); TLC (toluene/methyl ethyl ketone/glacial acetic acid (72:20:8)): Rf=0.66.

EXAMPLE 20

2-{5-[(2,5-Bis-(4-methylphenylmethoxy)phenyl)methylene]-4-oxo-2-thioxo-3-thiazolidine}-3-phenylacetic Acid Analogously to Example 1, from 2,5-bis-(4-methylphenylmethoxy)benzaldehyde and 2-(4-oxo-2-thioxo-3-thiazolidine)-2-phenylacetic, yield 67%.

¹HNMR (DMSO-d6, 250 MHz) δ 7.9 (s, 1H), 6.8–7.4 (m, 17H), 5.15 (s, 2H), 5.06 (s, 2H), 2.5 (s, 3H), 2.3 (s, 3H), TLC (toluene/methyl ethyl ketone/glacial acetic acid 72:20:8)): Rf=0.55.

EXAMPLE 21

2-{5-[(2,5-Bis-(4-methylphenylmethoxy)phenyl)methylene]-4-oxo-2-thioxo-3-thiazolidine}-propionic Acid Analogously to Example 1, from 2,5-bis-(4-methylphenylmethoxy)benzaldehyde and 2-(4-oxo-2-thioxo-3-thiazolidine)-propionic acid, yield 50%.

¹HNMR (DMSO-d6,250 MHz) δ 7.9 (s, 1H), 6.9–7.4 (m, 11H), 5.6 (q, 1H), 5.12 (s, 2H), 5.08 (s, 2H), 2,5 (s, 3H), 2.3 (s, 3H), 1.52 (d, 3H); TLC (toluene/methyl ethyl ketone/glacial acetic acid 72:20:8)): Rf=0.58.

EXAMPLE 22

2-{5-[(2,4-Bis-(4-methylphenylmethoxy)phenyl) methylene]-4-oxo-2-thioxo-3-thiazolidine}-2-phenylacetic Acid Analogously to Example 1, from 2,4-bis-(4-methylphenylmethoxy)benzaldehyde and 2-(4-oxo-2-thioxo-3-thiazolidine)-2-phenylacetic acid, yield 84%.

¹HNMR (DMSO-d6, 250 MHz) δ 7.95 (s, 1H), 6.75–7.5 (m, 17H), 5.21 (s, 2H), 5.12 (s, 2H), 2.5 (s, 3H), 2.3 (s, 3H), TLC (toluene/methyl ethyl ketone/glacial acetic acid 72:20:2)): Rf=0.30.

EXAMPLE 23

2-{5-[(2,4-Bis-(4-methylphenylmethoxy)phenyl) methylene]-4-oxo-2-thioxo-3-thiazolidine}-3-phenypropionic Acid Analogously to Example 1, from 2,4-bis-(4-methylphenylmethoxy)benzaldehyde and 2-(4-oxo-2-thioxo-3-thiazolidine)-3-phenylpropionic acid, yield 57%.

¹HNMR (DMSO-d6, 250 MHz) δ 7.88 (s, 1H), 6.75–7.4 (m, 16H), 5.85 (m, 1H), 5.20 (s, 2H), 5.15 (s, 2H), 3.45 (m, 2H), 2.5 (s, 3H), 2.3 (s, 3H); TLC (toluene/methyl ethyl ketone/glacial acetic acid 72:20:2)): Rf=0.27.

EXAMPLE 24

2-{5-[(2,4-Bis-(4-methylphenylmethoxy)phenyl) methylene]-4-oxo-2-thioxo-3-thiazolidine}-2-(4-chlorophenyl)acetic Acid Analogously to Example 1, from 2,4-bis-(4-methylphenylmethoxy)benzaldehyde and 2-(4-oxo-2-thioxo-3-thiazolidine)-2-(4-chlorophenyl)acetic acid, yield 63%.

¹HNMR (DMSO-d6,250 MHz) δ 7.95 (s, 1H), 6.75–7.55 (m, 16H), 5.21 (s, 2H), 5.15 (s, 2H), 2.5 (s, 3H), 2.3 (s, 3H); TLC (toluene/methyl ethyl ketone/glacial acetic acid (72:20:2)): Rf=0.25.

EXAMPLE 25

2-{5-[(2,4-Bis-(4-methylphenylmethoxy)phenyl) methylene]-4-oxo-2-thioxo-3-thiazolidine}-propionic Acid Analogously to Example 1, from 2,4-bis-(4-methylphenylmethoxy)benzaldehyde and 2-(4-oxo-2-thioxo-3-thiazolidine)-propionic acid, yield 56%.

¹HNMR (DMSO-d6,250 MHz) δ 7.93 (s, 1H), 6.75–7.45 (m, 11H), 5.6 (q, 1H), 5.21 (s, 2H), 5.15 (s, 2H), 2.5 (s, 3H); 2.3 (s, 3H), 1.5 (d, 3H); TLC (toluene/methyl ethyl ketone/glacial acetic acid (72:20:8)): Rf=0.56.

EXAMPLE 26

Biological Activity of the Novel Compounds

The compound of the invention were tested (ELISA test) as human urokinase (uPA) inhibitors, which bind to the specific receptor uPAR mAk (BIO-R₄), in accordance with the procedure described by Rettenberger et al. In Biol. Chem. Hoppe Seyler 376, 587–94 (1995). The assays are carried out in microtitre plates (96 wells).

Results:

| Compound | % Inhibition at 1 μg/ml concentration |
|---|---|
| Compound 2 | 48 |
| Example 2 | 68 |
| Example 6 | 57 |
| Example 13 | 53 |
| Example 15 | 63 |
| Example 22 | 60 |
| Example 23 | 54 |
| Example 24 | 69 |

What is claimed is:

1. A compound of formula I:

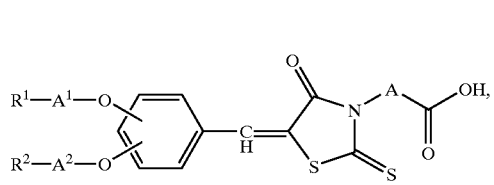

(I)

wherein

A is a linear $C_1$–$C_6$-alkylene chain or a group >CHR, wherein R is a $C_1$–$C_6$-alkyl residue, an aryl residue, an aralkyl residue or a carboxyalkyl residue, $A^1$ and $A^2$
  each independently in any combination are a linear or branched saturated or unsaturated $C_1$–$C_6$-alkylene chain, $R^1$ and $R^2$
  each independently in any combination are a group of formula II, formula III or formula IV,

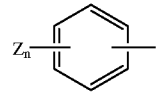

(II)

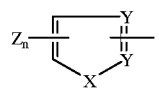

(III)

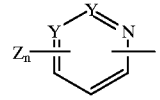

(IV)

wherein X is an oxygen or sulphur atom and each Y independently is a nitrogen or carbon atom, with the proviso that both Y's can not simultaneously be nitrogen, Z is a $C_1$–$C_4$-alkyl, aryl, aralkyl, heteroaryl, heteroaralkyl, $C_3$–$C_5$-alkenyl, $C_1$–$C_4$-alkoxy, $C_1$–$C_4$-alkylthio, acylamino, (alkyl)aminocarbonyl, $C_1$–$C_4$-alkyl-carbonyl, trifluoromethyl, difluoromethoxy, trifluoromethoxy, trifluoromethylthio, nitro, hydroxy or carboxy group or a chlorine, bromine or fluorine atom or the aromatic ring in formulae II-IV is substituted with a methylenedioxy or ethylenedioxy group and n is a whole number between 0 and 3,
whereby the Z substituents can be present in any positions,
with the proviso that the $R^1$-$A^1$- and $R^2$-$A^2$- residues can not simultaneously be an unsubstituted benzyl residue when A is a methylene group, or a pharmaceutically acceptable salt or ester of a compound of formula I, or a position isomer, optically active form, racemate or diastereomer mixture thereof.

2. A compound in accordance with claim 1, wherein A is a linear $C_1$–$C_6$-alkylene chain or a group >CH(R).

3. A compound in accordance with claim 2, wherein the compound is present in the (R) or (S) configuration or as a racemate when R is a linear $C_1$–$C_6$-alkyl residue, an aryl residue, an aralkyl residue or a carboxyalkyl residue.

4. A compound in accordance with claim 1, wherein $R^1$-$A^1$- and $R^2$-$A^2$- are independently an aralkyl group with a $C_1$–$C_4$-alkylene chain, a cinnamyl residue, a 2-thienylmethyl, a 3-thienylmethyl, a 2-furanylmethyl, a 3-furanylmethyl, a 2-thiazolylmethyl, a 4-thiazolylmethyl, a 2-oxazolylmethyl, a 4-oxazolylmethyl, a 3-isoxazolylmethyl or a 4-isoxazolylmethyl group or a homologue thereof with $C_2$–$C_4$-alkylene chains, whereby the respective aryl and heteroaryl residues of the aforementioned groups are unsubstituted or mono- or multiply-substituted by a substituent selected from Z.

5. A compound in accordance with claim 1, wherein $R^1$ and $R^2$ each independently are a phenyl group or a group of formula III or IV, wherein the groups $A^1$ and $A^2$ are methylene, 1,2-ethanediyl or 1,3-propanediyl and A is methylene, phenylmethylene, 2-phenylethane-1.1-diyl, 1,2-ethanediyl or 1,3-propanediyl, whereby the respective aryl and heteroaryl groups are unsubtistuted or substituted by a substituent selected from Z.

6. A compound in accordance with claim 1, 5-[(2,4-bis-(4-methylphenylmethoxy)phenyl)methylene]-4-oxo-2-thioxo-3-thiazolidineacetic acid.

7. A compound in accordance with claim 1, 5-[(2,5-bis-(4-methylphenylmethoxy)phenyl)methylene]-4-oxo-2-thioxo-3-thiazolidineacetic acid.

8. A compound in accordance with claim 1, 5-[(2,5-bis-(3-(4-chlorophenyl)propoxy)phenyl)methylene]-4-oxo-2-thioxo-3-thiazolidineacetic acid.

9. A compound in accordance with claim 1, 5-[(2-phenylmethoxy-5-(3-phenylpropoxy)phenyl)methylene]-4-oxo-2-thioxo-3-thiazolidineacetic acid.

10. A compound in accordance with claim 1, 5-[(2-(2-thienylmethoxy)-5-(3-phenylpropoxy)phenyl)methylene]-4-oxo-2-thioxo-3-thiazolidineacetic acid.

11. A compound in accordance with claim 1, 2-{5-[(2,4-bis-(4-methylphenylmethoxy)phenyl)methylene]-4-oxo-2-thioxo-3-thiazolidine}-2-phenylacetic acid.

12. A compound in accordance with claim 1, 2-{5-[(2,4-bis-(4-methylphenylmethoxy)phenyl)methylene]-4-oxo-2-thioxo-3-thiazolidine}-3-phenypropionic acid.

13. A compound in accordance with claim 1, 2-{5-[(2,4-bis-(4-methylphenyl-methoxy)phenyl)methylene]-4-oxo-2-thioxo-3-thiazolidine}-2-(4-chlorophenyl)acetic acid.

14. A method of treating colorectal or breast cancer, comprising administering to a patient in need of such treatment or prevention an effective amount of a compound of formula I,

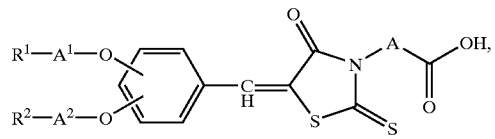

in which

A is a linear $C_1$–$C_6$-alkylene chain or a group >CHR, wherein R is a $C_1$–$C_6$-alkyl residue, an aryl residue, an aralkyl residue or a carboxyalkyl residue, $A^1$ and $A^2$ each independently in any combination are a linear or branched saturated or unsaturated $C_1$–$C_6$-alkylene chain, $R^1$ and $R^2$ each independently in any combination are a group of formula II, formula III or formula IV,

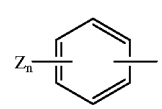

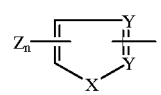

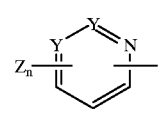

wherein X is an oxygen or sulphur atom and each Y is a nitrogen or carbon atom, with the proviso that boty Y's can not simultaneously be nitrogen, Z is a $C_1$–$C_4$-alkyl, aryl, aralkyl, heteroaryl, heteroaralkyl, $C_3$–$C_5$-alkenyl, $C_1$–$C_4$- alkoxy, $C_1$–$C_4$-alkylthio, acylamino, (alkyl)aminocarbonyl, $C_1$–$C_4$-alkyl-carbonyl, trifluoromethyl, difluormethoxy, trifluoromethoxy, trifluoromethylthio, nitro, hydroxy or carboxy group or a chlorine, bromine or fluorine atom or the aromatic ring in formulae II-IV is substituted with a methylenedioxy or ethylenedioxy group and n is a whole number between 0 and 3, whereby the Z substituents can by present in any positions, or a pharmaceutically acceptable salt or ester of a compound of formula I, or a position isomer, optically active form, racemate or diastereomer mixture thereof.

15. A method in accordance with claim 14, wherein A is a linear $C_1$–$C_6$- alkylene chain or a group >CH(R).

16. A method in accordance with claim 15, wherein the compound is present in the (R) or (S) configuration or as a racemate when R is a linear $C_1$–$C_6$-alkyl residue, an aryl residue, an aralkyl residue or a carboxyalkyl residue.

17. A method in accordance with claim 14, wherein $R^1$-$A^1$- and $R^2$-$A^2$- are independently an aralkyl group with a $C_1$–$C_4$-alkylene chain, a cinnamyl residue, a 2-thienylmethyl, a 3-thienylmethyl, a 2-furanylmethyl, a 3-furanylmethyl, a 2-thiazolylmethyl, a 4- thiazolylmethyl, a 2-oxazolylmethyl, a 4-oxazolylmethyl, a 3-isoxazolylmethyl or a 4- isoxazolylmethyl group or a homologue thereof with $C_2$–$C_4$-alkylene chains, whereby the respective aryl and heteroaryl residues of the aforementioned groups are unsubstituted or mono- or multiply-substituted by a substituent selected from Z.

18. A method in accordance with claim 14, wherein $R^1$ and $R^2$ each independently are a benzyl group, a 2-phenethyl group, a 3-phenylpropyl group or a group of formula III or IV, wherein the groups $A^1$ and $A^2$ are methylene, 1,2-ethanediyl or 1,3-propanediyl and A is methylene, phenylmethylene, 2-phenylethane-1.1-diyl, 1,2-ethanediyl or 1,3- propanediyl, whereby the respective aryl and heteroaryl groups are unsubtistuted or substituted by a substituent selected from Z.

19. A method in accordance with calim 18, wherein the compound is 5-[(2,4-bis -(4- methylphenylmethoxy)phenyl) methylene]-4-oxo-2-thioxo-3-thiazolidineacetic acid.

20. A method in accordance with claim 18, wherein the compound is 5-[(2,5-bis-(4- methylphenylmethoxy)phenyl) methylene[-4-oxo-2-thioxo-3-thiazolidineacetic acid.

21. A method in accordance with claim 18, wherein the commpound is 5-[(2,5-bis- (3-(4-chlorophenyl)propoxy) phenyl)methylene[-4-oxo-2-thioxo-3-thiazolidineacetic acid.

22. A method in accordance with claim 18, wherein the compound is 5-[(2- phenylmethoxy-5-(3-phenylpropoxy) phenyl)methylene[-4-oxo-2-thioxo-3-thiazolidineacetic acid.

23. A method in accordance with claim 18, wherein the compound is 5-[(2-(2- thienylmethoxy)-5-(3-phenylpropoxy)phenyl)methylene[-4-oxo-2-thioxo-3-thiazolidineacetic acid.

24. A method in accordance with claim 18, wherein the compound is 2-{5-[(2,4-bis- (4-methylphenylmethoxy) phenyl)methylene[-4-oxo-2-thioxo-3-thiazolidine}-2-phenylacetic acid.

25. A method in accordance with claim 18, wherein the compound is 2-{5-[(2,4-bis- (4-methylphenylmethoxy) phenyl)methylene[-4-oxo-2-thioxo-3-thiazolidine}-3-phenypropionic acid.

26. A method in accordance with claim 18, wherein the compound is 2-{5-[(2,4-bis- (4-methylphenylmethoxy) phenyl)methylene[-4-oxo-2-thioxo-3-thiazolidine}-2-(4-chlorophenyl)acetic acid.

* * * * *

UNITED STATES PATENT AND TRADEMARK OFFICE
CERTIFICATE OF CORRECTION

PATENT NO. : 6,506,755 B2
DATED : January 14, 2003
INVENTOR(S) : Walter-Gunar Friebe et al.

It is certified that error appears in the above-identified patent and that said Letters Patent is hereby corrected as shown below:

<u>Column 16,</u>
Line 38, delete "boty" and insert -- both --.

<u>Column 17,</u>
Line 13, delete "calim" and insert -- claim --.

Signed and Sealed this

Thirteenth Day of May, 2003

JAMES E. ROGAN
*Director of the United States Patent and Trademark Office*